(12) United States Patent
Wyatt (10) Patent No.: US 6,411,383 B1
(45) Date of Patent: Jun. 25, 2002

(54) METHOD FOR MEASURING THE $2^{ND}$ VIRIAL COEFFICIENT

(75) Inventor: Philip J. Wyatt, Santa Barbara, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 09/752,593

(22) Filed: Dec. 22, 2000

(51) Int. Cl.$^7$ .............................................. G01N 21/00
(52) U.S. Cl. ..................... 356/338; 356/336; 356/337; 356/340; 356/341; 250/574; 250/575
(58) Field of Search ................... 356/335, 336, 356/337, 338, 339, 340, 341, 342, 343, 344; 250/574, 575; 702/292, 101.31, 282

(56) References Cited

U.S. PATENT DOCUMENTS

| | | | | |
|---|---|---|---|---|
| 4,693,602 A | * | 9/1987 | Wyatt et al. | 356/336 |
| 5,129,723 A | * | 7/1992 | Howie et al. | 356/336 |
| 5,528,366 A | * | 6/1996 | Shortt | 356/344 |
| 5,530,540 A | * | 6/1996 | Wyatt et al. | 356/338 |
| 6,052,184 A | * | 4/2000 | Reed | 356/338 |
| 6,216,091 B1 | * | 4/2001 | Hammond | 702/23 |
| 6,219,138 B1 | * | 4/2001 | Swanson et al. | 356/336 |

* cited by examiner

Primary Examiner—Frank G. Font
Assistant Examiner—Sang H. Nguyen
(74) Attorney, Agent, or Firm—Philip J. Wyatt (57) ABSTRACT

A method is described to determine the $2^{nd}$ virial coefficient of an ensemble of molecules dissolved in a selected solvent. Two distinct classes are described: monodisperse and polydisperse molecules. If the molecules are monodisperse, they must be prepared for a chromatographic separation and suitable columns selected. Following standard chromatographic separation procedures such as exemplified by the method of size exclusion chromatography, the sample passes through the separation columns, a multiangle light scattering detector, and a concentration detector. The effect of the columns is to produce a concentration profile of said sample that appears as a peak as it passes through the light scattering and concentration detectors. For each elution interval, $v_i$, a corresponding concentration value $c_i$ and set of excess Rayleigh ratios $R_i(\theta_j)$ is measured for each scattering angle $\theta_j$. The excess Rayleigh ratios are extrapolated to $\theta = 0°$ resulting in the calculation of a single extrapolated value for each elution slice, viz., $R_i(0°)$. Three sums are calculated from the data collected: 1) the sum of all $c_i$ values over the measured concentration peak; 2) the sum of all $(c_i)^2$ values over the same concentration peak; and 3) the sum of all the extrapolated Rayleigh ratios over the measured light scattering peak. The $2^{nd}$ virial coefficient may be calculated directly from these three quantities once the molecule's molar mass is known. The same procedure is followed for polydisperse samples, however, the column set is replaced by a dilution means that does not fractionate the sample.

24 Claims, 11 Drawing Sheets

METHOD FOR MEASURING THE $2^{ND}$ VIRIAL COEFFICIENT

BACKGROUND

Molecules in solution are generally characterized by their weight averaged molar mass, their mean square radius, and the second virial coefficient; the latter being a measure of the interaction between the molecules and the solvent. For unfractionated solutions, these properties may be determined from measurement of the manner by which they scatter light following the method described by Bruno Zimm in his seminal 1948 paper which appeared in the Journal of Chemical Physics, volume 16, pages 1093 through 1099. Basically, the light scattered from a small volume of the solution is measured over a range of angles and concentrations. The properties derived from the light scattering measurements are related through the formula developed by Zimm, as follows:

$$R(\theta)/K^* = M_W c P(\theta)[1 - 2A_2 M_W c P(\theta)] + O(c^3) + L, \quad (1)$$

where $M_W$ is the weight average molar mass, $R(\theta)$ is the measured excess Rayleigh ratio, $P(\theta)$ is the form factor of the scattering molecules, $K^* = 4\pi^2 (dn/dc)^2 n_0^2/(N_a \lambda_0^4)$, $N_a$ is Avogadro's number, $(dn/dc)$ is the refractive index increment, $n_0$ is the solvent refractive index, and $\lambda_0$ is the wavelength of the incident light in vacuum. The collection of light scattering data over a range of scattering angles is referred to more commonly as multiangle light scattering, or by the acronym MALS. The data so-collected are then extrapolated to vanishingly small concentrations and 0° scattering angles by means of the so-called Zimm plot technique. For this purpose, the reciprocal of Eq. (1) is more commonly used which, through order $c^2$, may be written as follows:

$$K^* c/R(\theta) = 1/[M_W P(\theta)] + 2A_2 c. \quad (2)$$

The Zimm plot technique was developed primarily for binary solutions comprised of a simple solvent and the molecular solute. To apply the technique to more complex solvents containing buffering salts, for example those used for the study of proteins by light scattering, the solutions must be dialyzed at each measured concentration. For these latter solutions, the procedure is both labor and time intensive.

A more powerful means by which a molecular solution may be analyzed is to fractionate the sample first by chromatographic means, such as size exclusion chromatography or SEC, and then perform a Zimm plot on each eluting fraction or slice. Because such SEC separations are subject to very large dilutions, the sample concentration is so small at the time the light scattering measurement is performed that the need to extrapolate to vanishingly small concentrations is obviated since the concentration is already almost negligible. The only extrapolation required is that to zero scattering angle which is easily performed by software such as the ASTRA® software developed by Wyatt Technology Corporation of Santa Barbara, Calif. However, this approach is tantamount to assuming $A_2=0$, which essentially precludes its determination.

There are several advantages to this fractionation approach in addition to the obvious simplifications of the Zimm technique. First is the ability of the combined fractionation/MALS measurement to permit calculation of the distributions of molar mass and mean square radius over the entire sample. From these distributions, their associated moments, such as the weight averaged, number averaged, and z-averaged molar mass and sizes, may be calculated. Details of the chromatographic separation methods, the definitions and calculations of the mass and size moments, and an explanation of the terminology used to describe the associated distributions may be found in the 1993 review article by Wyatt in Analytica Chimica Acta, volume 272, pages 1 through 40. It should be noted that the weight average molar mass of the sample calculated from the fractionated sample measurements should be nearly identical to the corresponding weight average molar mass generated from batch measurements performed by the Zimm plot technique. A small discrepancy between the two methods is due to the setting of $A_2=0$ in the chromatographic approach. Another benefit of such measurement is that the sample undergoing SEC fractionation is being dialyzed throughout its separation permitting, thereby, MALS measurement with buffered solutions. Unfortunately, since the molecular solute was assumed to be at a vanishingly small concentration, in general there has been no means to recover the second virial coefficient for the solvent/solute interaction. Indeed, until the development of the present invention, the only means by which the $2^{nd}$ virial coefficient could be derived was from the analysis of unfractionated samples following the Zimm plot technique.

In U.S. Pat. No. 5,129,723 by Howie, Jackson, and Wyatt, a method was described whereby an unfractionated sample was injected into a MALS detector following dilution and thorough mixing. This procedure produced a sample peak passing through the light scattering detector whose profile was assumed proportional to the concentration profile of the diluted, yet unfractionated, sample. Since the mass distribution at each slice was the same, it was assumed that each point of the profile was proportional, at that point, to the sample's concentration times the weight averaged molar mass by referring to Eq. (2) and setting $A_2=0$. On this basis, a Zimm plot could be produced using a set of these points and the associated weight average molar mass, mean square radius, and $2^{nd}$ virial coefficient were then derived. A concentration detector was not needed, since knowledge of the total mass injected was sufficient to convert the sample peak curve into a concentration profile. The method was flawed because the assumption that $A_2$ was zero contradicted the derived result that it was not. Selecting concentration points from the ascending or descending parts of the peak yielded different results while using concentration points from both sides produced extremely poor and inconsistent Zimm plots.

Returning to the fractionation/dialysis approach for the case of a protein sample, we note that the weight average molar mass at each eluting fraction should be constant throughout the elution peak since, absent aggregation, the protein mass distribution is monodisperse. Even in the presence of aggregates, the separation method should be developed to separate such aggregates from the protein monomer. With the addition of a concentration monitor, such as a differential refractive index detector, an evaporative light scattering detector, or UV detector, once the delay volume between the light scattering and concentration detectors has been established, both the light scattering and concentration signals will be known at each eluting fraction or slice. The delay volume may be determined, for example, by the method described by Wyatt and Papazian in their 1993 paper appearing in volume 11, pages 862 through 872 of the trade journal LC-GC. From the thus-corrected MALS and concentration data, a Zimm plot might be generated from values at several different slices or sets of slices of the elution profile. On this basis, the weight average molar mass and $2^{nd}$ virial coefficient may be derived therefrom. In general, the root mean square radius for most proteins will be too small to be derived from said Zimm plot.

There remains a relatively small, though important, distortion associated with Zimm plots derived in this manner: because of band broadening effects, the actual concentration profile will appear slightly flattened, i. e. spread out. The term "band broadening" refers to the observed broadening of a peak's breadth due to the presence of the additional dead volumes between detectors. Part of such a broadening effect arises from the delay volume itself, though this is usually small compared to the larger dead volume, for example, of the DRI detector needed to assure thermal equilibrium of the samples passing therethrough. Because of the slight distortions of the resultant concentration profile, the derived mass distribution will no longer be calculated as monodisperse despite the monodispersity of the protein sample. The other properties derived, such as the $2^{nd}$ virial coefficient, will contain also some deviations from their true values because of this effect. Since the $2^{nd}$ virial coefficient is generally very small, it produces a relatively small contribution to the final mass calculation. But the error associated with band broadening upon the mass calculation is a comparably small quantity and so one would expect that such band broadening could affect the $2^{nd}$ virial coefficient calculation significantly. Various analytical corrections of such band broadening have been developed over the years, but they are not without their own problems. Even were such corrections made suitably, the need to make a Zimm plot solely for the purpose of measuring the $2^{nd}$ virial coefficient of a particular protein-solvent interaction is time consuming. Since the protein molar mass for a monodisperse sample in a suitable buffering solvent is easily measured by MALS, mass spectroscopy, or direct sequencing, it would be useful to circumvent the Zimm plot altogether and measure the $2^{nd}$ virial coefficient directly. This would speed up the measurement process considerably and permit the examination of many solvent/protein combinations to derive conditions for protein crystallization or solubility. Such determinations are essential to provide a better understanding of protein processes. A particular beneficiary of such rapid measurements would be the field of combinatorial chemistry. It is a major objective of this invention to show a new means by which such determinations may be achieved.

SUMMARY OF THE INVENTION

This invention concerns a method by which the $2^{nd}$ virial coefficient of a sample comprised of a monodisperse molar mass distribution in a solvent may be determined directly. The same method may be applied to certain classes of unfractionated samples. It is of particular importance in the field of protein chemistry wherein light scattering techniques are applied to measure molar mass interactions with complex buffered solvents and require that samples be dialyzed against such solvents prior to such measurement.

The method, applied to the exemplar of a monodisperse protein sample, begins with the preparation of the sample for injection onto a SEC column set. Following the columns, a MALS detector and concentration detector are connected serially. For small molecules whose mean square radii are too small to measure, measurement at a single scattering angle, such as 90° may suffice, though the precision of the determination may be diminished. These are the conventional elements of a standard separation by SEC means resulting in an absolute determination of the eluting molar masses present in the sample. Unlike this conventional measurement procedure, the direct determination of the $2^{nd}$ virial does not require correction for the delay volume between detectors nor is it affected by the presence of band broadening.

From the measurement of the concentration, $c_1$, at each slice i, the square of this quantity, $c_i^2$, is calculated. The total eluted mass, m, is then calculated by integrating the area under the concentration detector response peak as a function of elution volume. The excess Rayleigh ratios for each scattering angle are extrapolated to zero scattering angle and the sums $$\sum_i R_i(0°)\Delta v_i / K^*, \quad \sum_j c_j \Delta v_j,$$

and $$\sum_j c_j^2 \Delta v_j$$

are calculated, where $\Delta v_i$ is the incremental elution volume of slice i. Note that the contributions to the summations over $c_j$ and $c_j^2$ may include a greater number of slice contributions than the sums over the excess Rayleigh ratios since the concentration peak is often broadened due the presence of band broadening. For the case of equidistant slices, i. e. when $\Delta v_i = \Delta v =$ constant, the sums calculated are simplified to $$\sum_i R_i(0°)/K^*, \quad \sum_j c_j \Delta v_j,$$

and $$\sum_j c_j^2 \Delta v_j.$$

From these measurements and calculations, the $2^{nd}$ virial coefficient may be derived immediately.

DETAILED DESCRIPTION OF THE INVENTION

Figure 1:
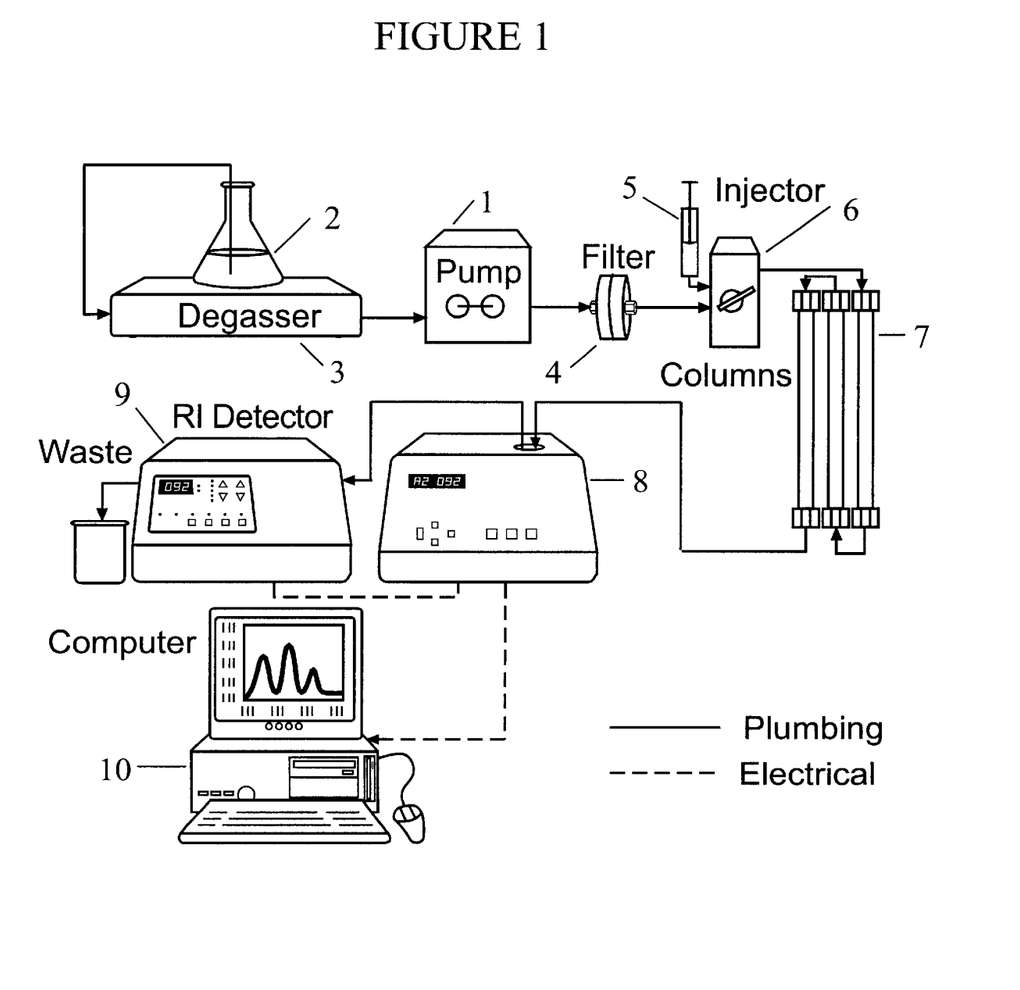
FIG. 1 shows the connections of the key chromatographic elements of the preferred embodiment of the invention.

In order to measure the $2^{nd}$ virial coefficient directly, a chromatographic separation including an associated dialysis is performed as indicated by the combined elements of FIG. 1. Solvent is drawn by pumping means 1 from a solvent reservoir 2 through a degasser 3 and then pumped through filter means 4. The degasser 3 is generally used to remove dissolved gasses from the solvent as such gasses might produce subsequently small bubbles in solution that could interfere with the desired measurements from the solution itself. Filter means 4 is generally incorporated as shown to remove residual particulate material from said solvent that could interfere also with the desired measurements. The sample 5, whose $2^{nd}$ virial is to be derived by the method of this invention, is injected by injector means 6 and, therefrom, passes through the selected column set 7 wherein it is dialyzed and/or fractionated and passed through light scattering MALS means 8. After said sample 5 has passed through MALS means 8, it flows through concentration detection means 9 whereby the sample concentration is detected at each slice interval $\Delta v_i = \Delta v$. The resultant light scattering and concentration signals are then stored and processed by computer means 10 to obtain the excess Rayleigh ratios, $R_i(\theta_{76})$, for each slice i at each scattering angle $\theta_t$. Computer means 10 also generates the molecular characteristics including mass and size and the distributions thereof. Sample concentration detector means 9 is generally a DRI differential refractive index detector though often an ultraviolet, UV, absorption detector is substituted therefore. An evaporative light scattering detector may be used alternatively to monitor the eluting sample's concentration though such device may need special calibration as its response is generally non-linear.

As a simple example, consider a very small protein molecule whose size is below the resolution limit of a light scattering measurement. Thus, for vertically polarized incident light, the scattering will be isotropic, i. e. $P(\theta)=1$ for all scattering angles $\theta$. For this case, the light scattering measurement at each angle will be the same. The extrapolated to $\theta=0°$ excess Rayleigh ratio, $R(0°)$ could be determined equally at $\theta=90°$ or at any set of angles, averaging over them to improve the signal-to-noise ratio. Let $\xi = R(0°)/K^*$. Equation (1) becomes $$\xi = Mc - 2A_2 M^2 c^2 \qquad (2)$$

since $P(0°)=1$. For $A_2=0$, the excess Rayleigh ratio divided by $K^*$ is seen to be equal to the product of molar mass (g/mol) and the concentration (g/ml). We shall refer to $\xi$ as the light scattering response. For the case of larger molecules whose corresponding scattering is not isotropic, the extrapolated values, $R(0°)/K^*$ for each slice must be derived analytically by software means.

Figure 2:
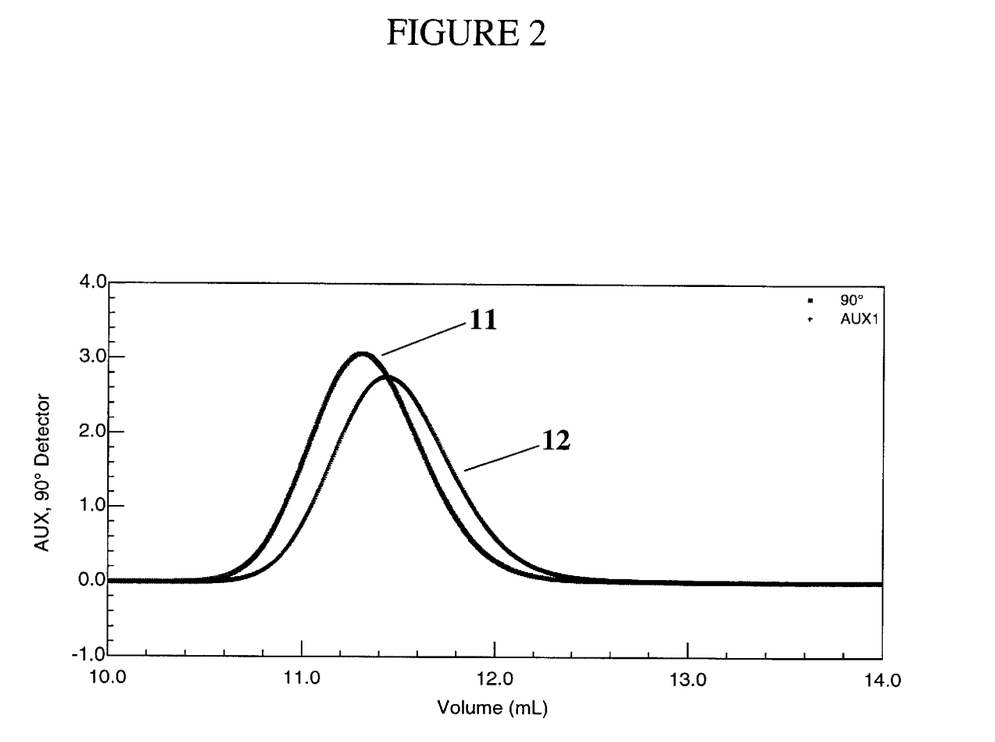
FIG. 2 shows a typical elution curve from the 90° light scattering detector and the corresponding signal from a DRI detector. The delay volume is uncorrected.
Figure 3:
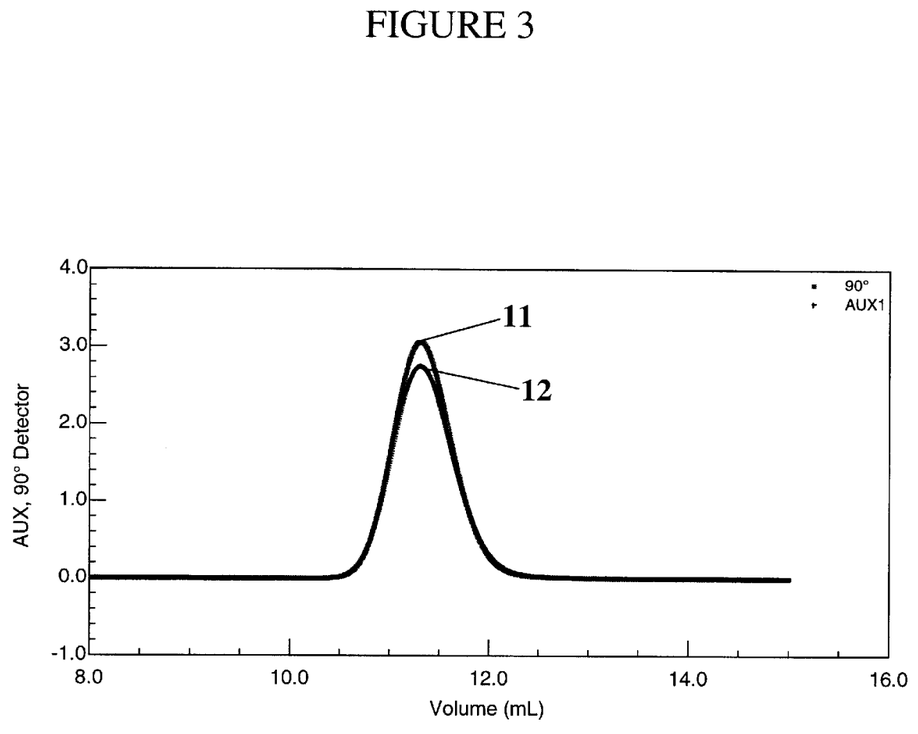
FIG. 3 shows the data of FIG. 2 following correction for the delay volume.
Figure 4:
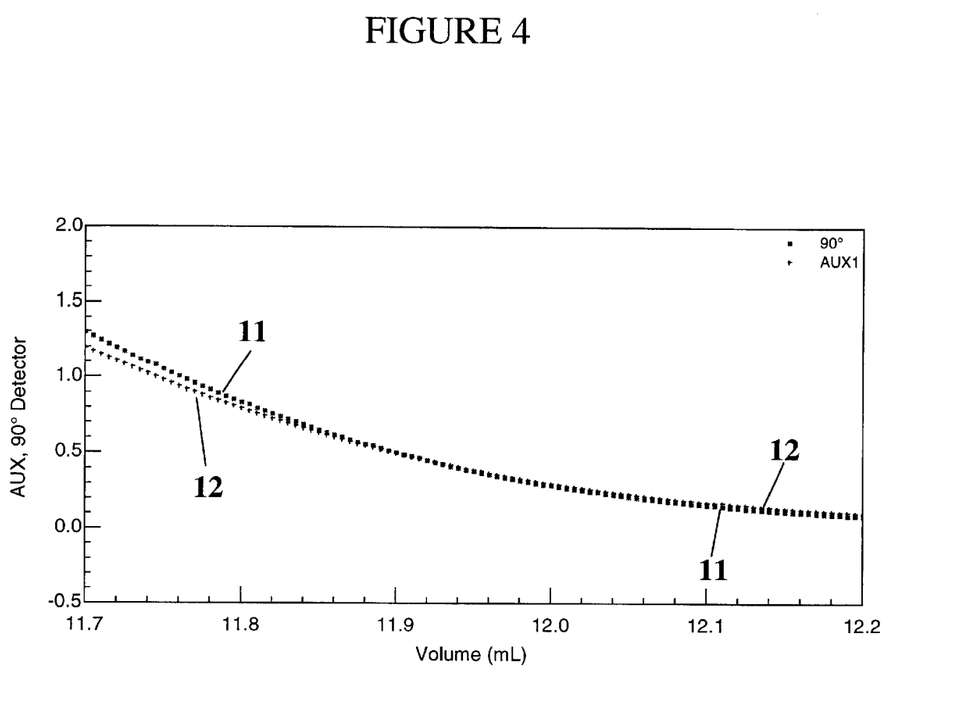
FIG. 4 shows a section of the curves of FIG. 3 indicative of slight band broadening.

Each light scattering detector produces a response at each angle similar to that shown 11 in FIG. (2) for scattering at $\theta=90°$ following elution from a GPC column set. Also shown in FIG. (2) is the corresponding trace 12 of the differential refractive index, or DRI, detector. It is difficult to see the fine detail of FIG. 2, but, after correcting for the delay between the detectors, the DRI signal is seen to be slightly depressed in the peak region of the LS signal and then rise slightly in the wings because of the previously mentioned band broadening. FIG. 3 shows the 90° light scattering peak 11 superimposed upon the DRI peak 12 following correction for the delay of the DRI signal with respect to the LS signal. FIG. 4 shows an enlarged view of a small section of these overlapping peaks with the afore-referenced broadening of the DRI signal 12 relative to the LS signal 11 clearly indicated. Said broadening results in a slightly greater mass calculated, using Eq. (1), for the peak region and a smaller mass calculated out in the wings. This is clearly shown in FIG. 5 where the calculated molar mass 13 and the DRI peak 12 are plotted against elution volume. Note that because of this slight band broadening, the DRI trace 12 of FIG. 4 is slightly broader than the LS trace 11 despite the fact that the sample (protein) is monodisperse. Applying Eq. (1) thus produces the downward-bowed mass response curve 13. Because of this, it will not be feasible to make a Zimm plot using the range of concentrations measured by the DRI as said concentrations are distorted, relative to what they should be, because of band broadening. The accurate determination of the $2^{nd}$ virial coefficient, $A_2$, requires accurate concentration values corresponding to each LS value.

Figure 6:
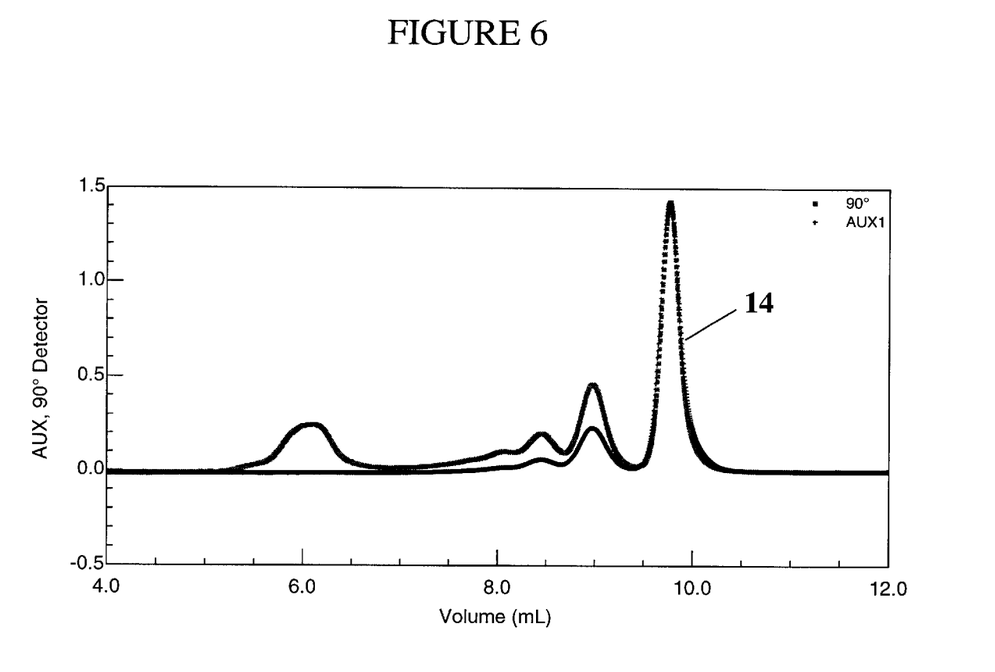
FIG. 6 shows the chromatogram of a BSA sample showing the presence various aggregates to the left of the monomer peak.
Figure 7:
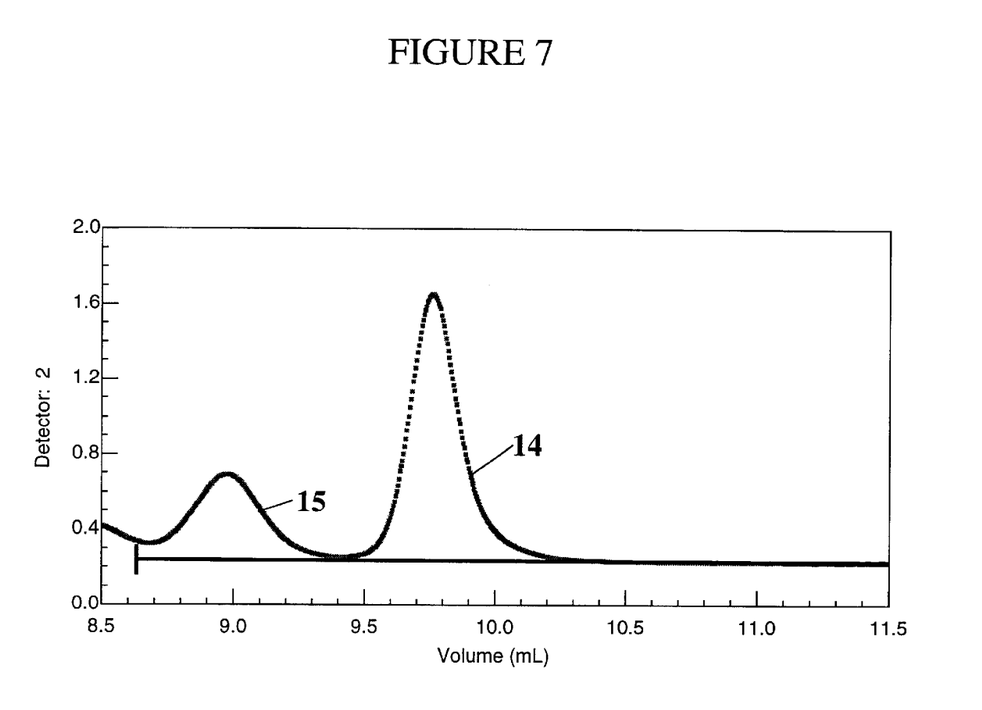
FIG. 7 shows the 90° light scattering response for the region between the monomer and dimer peaks relative to the light scattering baseline.
Figure 8:
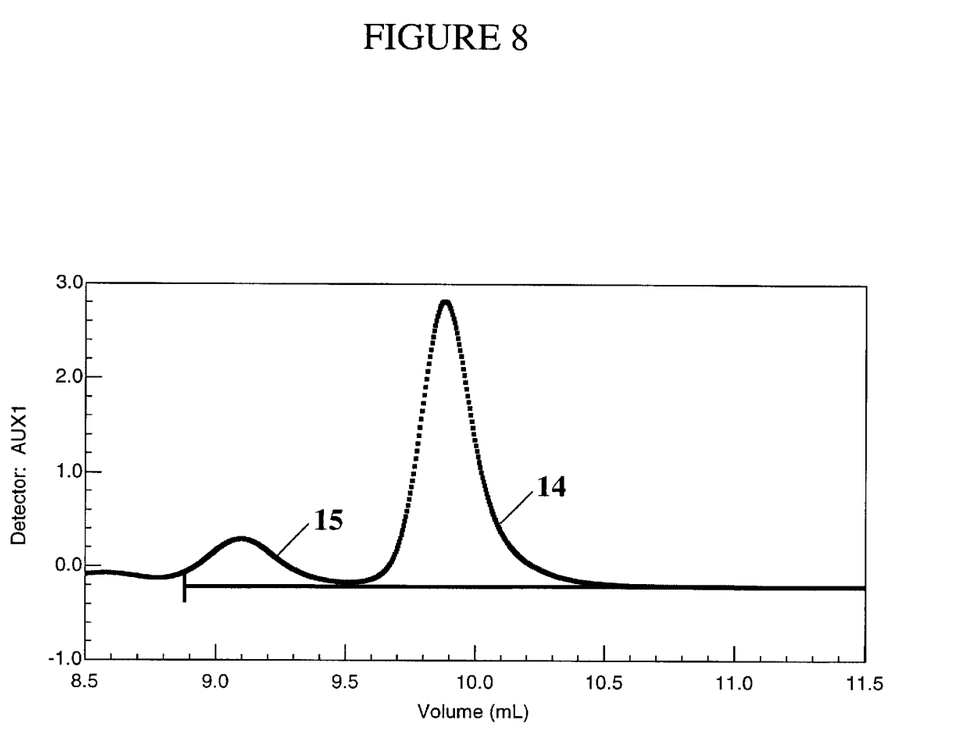
FIG. 8 shows the DRI response for the region between the monomer and dimer peaks relative to the DRI baseline.
Figure 9:
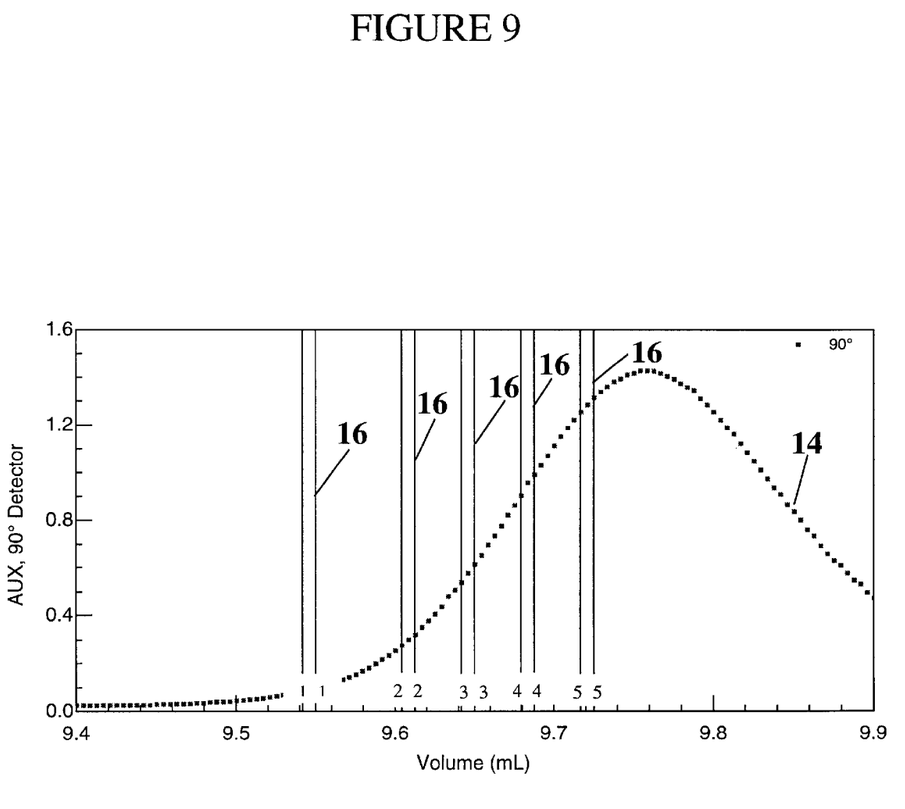
FIG. 9 shows the leading edge of the BSA monomer peak with the five peak regions that will form the basis for a Zimm plot.
Figure 10:
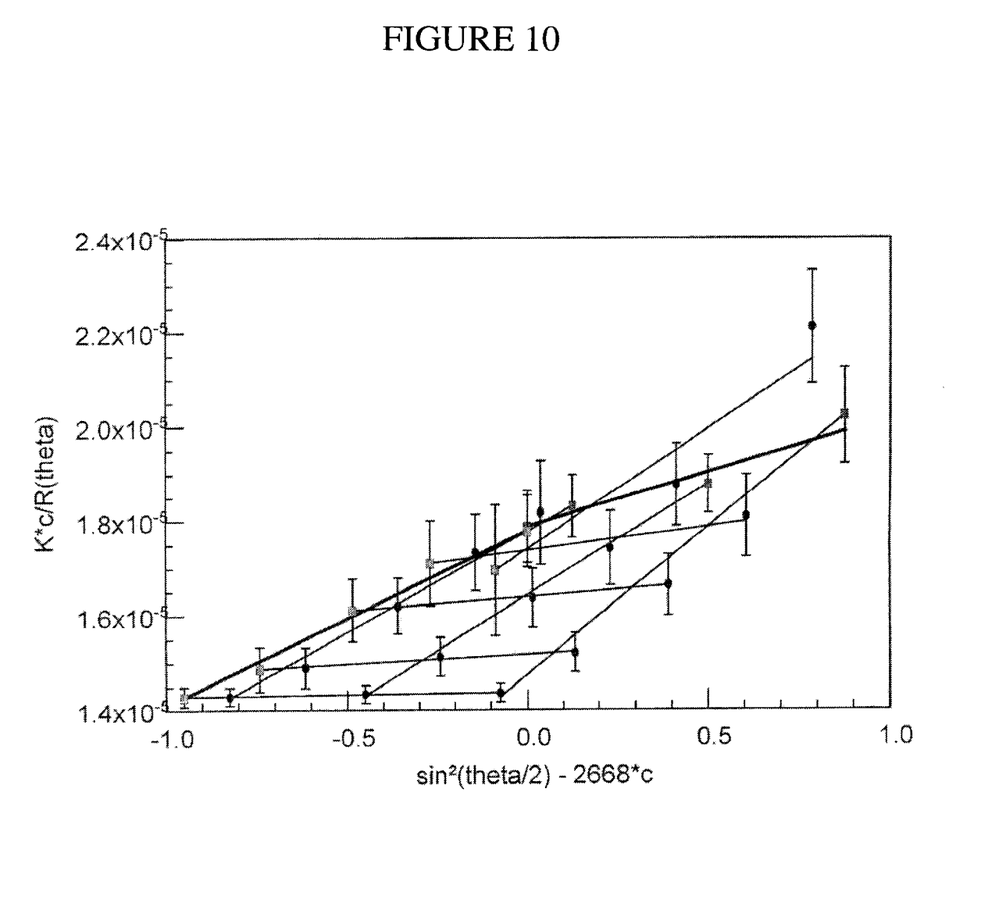
FIG. 10 is the Zimm plot generated from five averaged peak regions of FIG. 9 and their corresponding five averaged concentrations.

FIG. 6 shows the complete chromatogram for a sample of bovine serum albumin, BSA. The monomer peak 14 is at about 9.75 ml. The other peaks shown correspond to various aggregation states. The region between the dimer peak 15 and the monomer peak 14 is shown in FIGS. 7 and 8 for the 90° light scattering and DRI signals, respectively. Also shown in these figures are the associated baselines. The separation was achieved using an aqueous phosphate buffered saline solvent and an SEC column set from Showa Denko of Tokyo, Japan. A set of five regions 16 on the leading edge of the monomer peak 15 is shown in FIG. 9. These were used to generate the Zimm plot shown in FIG. 10. These regions are averaged over their three contributing slices shown together with the corresponding average concentration values from the DRI. The values derived therefrom of $M_w$, the root mean square radius $r_g$, and the $2^{nd}$ virial coefficient $A_2$ are listed in Table 1. The estimated errors were calculated following the method of Shortt in his U.S. Pat. No. 5,528,366. If a similar set of slices were selected from the trailing edge of the peak, an equally poor Zimm plot is produced.

TABLE 1

Results for the BSA monomer

| Method | $M_w$ | $r_g$ | $A_2$ |
|---|---|---|---|
| Zimm plot from SEC | (5.607 ± 0.34) × 10⁴ | 25.7 ± 8.6 nm | (−4.94 ± 1.17) × 10⁴ |
| SEC + MALS ($A_2 = 0$) | (6.633 ± 0.069) × 10⁴ | 4.8 ± 8.8 nm | NA |

The errors associated with the aforementioned example of a Zimm plot performed for an eluting monodisperse polymer are typical of the attempt to extract molecular parameters using the Zimm procedure. The data are sparse, the concentrations far below those needed for accurate Zimm plots, and band broadening effects in particular all tend to distort the plot and the final results derived therefrom. Until the present invention, as presently disclosed, the only precise means for calculating the $2^{nd}$ virial coefficient was to perform an off-line Zimm plot using higher concentrations and, for proteins, labor intensive dialysis procedures at each concentration. It should be noted also that the value of the $2^{nd}$ virial coefficient itself is extremely small, especially near theta conditions where it equals zero, which is a region of great importance.

Let us return now to Eq. (2) and integrate the light scattering peak over all elution incremental volume slices $\Delta v_i$=a constant value $\Delta v$ in a typical measurement. Thus $$\sum_i \xi_i = \sum_j M c_j - 2A_2 \sum_j M^2 c_j^2, \quad (3)$$

where the common factor $\Delta v$ has been removed for each sum.

The summation on the left hand side of Eq. (3), times the factor $\Delta v$, is just the area under the light scattering peak divided by $K^*$. Let us call it $$I = \sum_i \xi_i$$

which may be calculated directly. Note that the indices over the light scattering peak is indicated by the subscript i while that over the sums involving the concentrations are over a different index j. This is because the band broadening may spread the concentration peak over more incremental intervals. Thus $$\sum_i \xi_i = mM - 2A_2 M^2 \sum_j c_j^2, \quad (4)$$

where $m$, times the factor $\Delta v$, $= \sum_j c_j$ is the total mass eluted and the weight average molar mass $M_w$ has been determined earlier or, for the case of a protein, by sequencing.

Since the concentration detector, a DRI detector in this example, yields $c_i$ at each elution volume, we may easily calculate the last sum of Eq. (4) over the entire broadened range of the DRI. Let $$\sum_i c_i^2 = D$$

which may be calculated immediately. Thus the $2^{nd}$ virial coefficient may be obtained directly from Eq. (4) as $$A_2 = \frac{Mm - I}{2M^2 D}. \quad (5)$$

The result of Eq. (5) requires that the sample be comprised of a single molar mass such as is typical for non-aggregated proteins. In the event that such protein samples contain aggregates, it is important to derive suitable separation means so that the protein monomer peak and its corresponding concentration peak are baseline-separated from those of the aggregates. By baseline, we refer to the scattering from the pure solvent. The Rayleigh ratios are calculated by first subtracting the pure solvent light scattering values from the measured solution values. Details are given in the earlier cited article by Wyatt in Analytica Chimica Acta.

For samples comprised of polydisperse molecules an unseparated peak, obtained in the manner described by Howie et al., their $2^{nd}$ virial coefficients may be determined similarly. Note, however, that in contrast to the method of Howie et al., a sequential concentration detector is required for such samples.

Equation (5) contains the essence of the invention. Of particular importance is the measurement and calculation of m and D over a range of elution slices sufficient to include all elements of the eluting sample. The number of slices included in these sums generally will be greater than the number of slices used in the calculation of the sum I due to the effects of band broadening discussed previously. It is of further importance to insure that the sum D does not include terms that are statistically meaningless. As the values of the measured $c_i$ approach zero, they will fluctuate about the baseline values with both positive and negative contributions. Statistically, they will make no net contribution to the sum m. However, if the summation for D be extended beyond the statistically meaningful range, both positive and negative values will make positive contributions to the sum D wherein the squares of the measured values are added. It is important, therefore that the sum m be used to establish the meaningful range for slices whose contributions are added to D.

TABLE 2

Results for the BSA monomer by the method of the present invention.

| M | dn/dc | m | I | D | $A_2$ |
|---|---|---|---|---|---|
| $6.70 \times 10^4$ | 0.185 | $2.395 \times 10^{-2}$ | 1568 | $5.991 \times 10^{-6}$ | $6.81 \times 10^{-4}$ |
| $6.65 \times 10^4$ | 0.185 | $2.395 \times 10^{-2}$ | 1568 | $5.991 \times 10^{-6}$ | $4.66 \times 10^{-4}$ |

Figure 5:
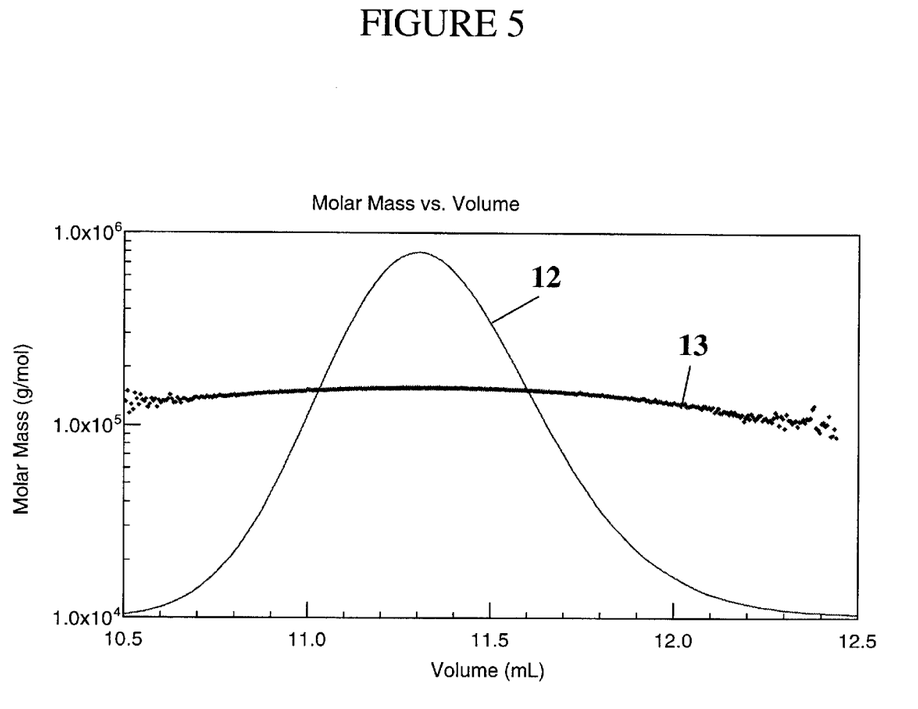
FIG. 5 shows the calculated mass profile of a protein monomer across the elution peak showing the effect of band broadening.
Figure 11:
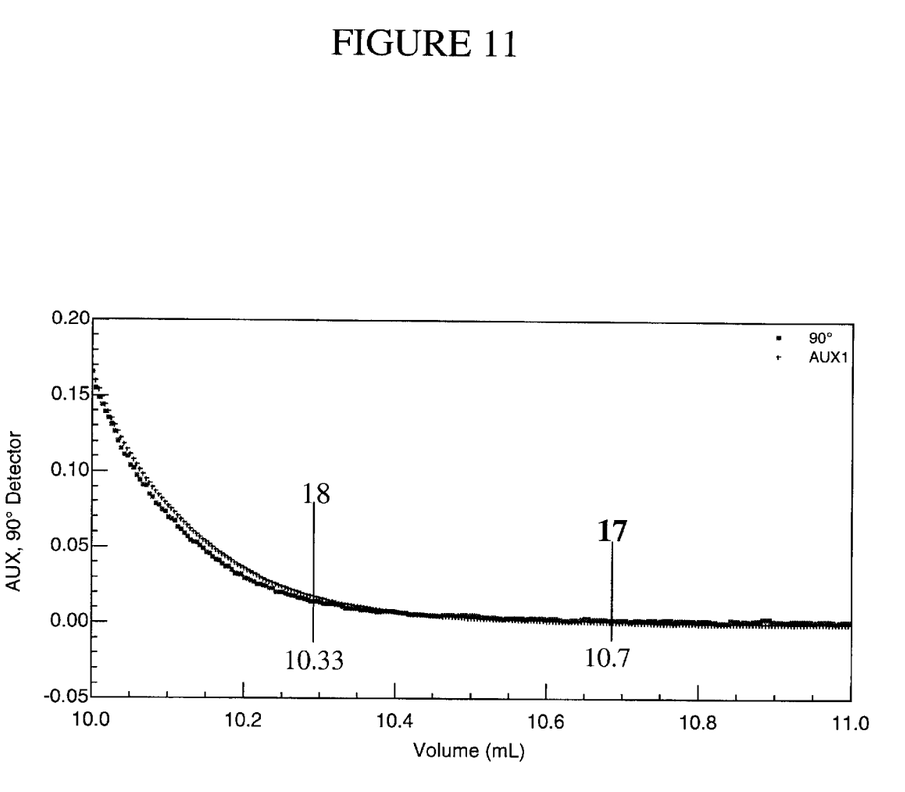
FIG. 11 shows the trailing edge of the DRI and light scattering monomer peak and the corresponding upper summation limits for the light scattering signals and the band broadened DRI signal.

Table 2 shows the results of the application of this invention to the determination of the $2^{nd}$ virial coefficient for the BSA monomer 14 of the sample used to generate FIGS. 6 through 9. Note that the concentration and 90° light scattering monomer peaks of FIGS. 7 and 8 are not baseline resolved and, therefore, the contributions to the summations near the beginning of the monomer peak has been slightly truncated. Both ranges over which the concentration values were selected to form the sums m and D and the excess Rayleigh ratios to form the sum I were set at an elution volume of 9.54, avoiding contributions from the adjacent dimmer peak. The concentration and Rayleigh ratios summations are, however, carried out to different limits because of the band broadening effects discussed earlier. These two limits are indicated by the indicial marks 17 and 18, respectively, shown in FIG. 11. The $2^{nd}$ virial coefficient, $A_2$, listed in Table 2 might be somewhat erroneous because of possible contributions from the unresolved tail of the dimer 15 into the monomer 14 peak. Note also that if the BSA monomer mass were selected at its known sequence value of $6.65 \times 10^4$ instead of $6.70 \times 10^4$, the $2^{nd}$ virial coefficient would decrease by 32%! The effect of band broadening on the calculated molar mass as seen in FIG. 5, though relatively small, nevertheless can play a significant role on the derived $2^{nd}$ virial coefficient were such to be derived directly from Zimm plots extracted from SEC measurements by the procedures illustrated by FIGS. 9 and 10. The accurate determination of the $2^{nd}$ virial coefficient, therefore, requires great care in the calculation of all pertinent quantities.

Establishing the summation limits for the quantities I, m, and D requires first that all baselines be accurately located. Once this is done, the slice-by-slice values for the light scattering and concentration signals must be examined to establish summation limits on both sides of the corresponding peak. For the trailing side of the peak, for example, all values should be kept until the decreasing values depart from a monotonic behavior and begin to fluctuate. Once a few values appear reversing the monotonic trend, the associated summation is stopped. Similar remarks apply to the ascending side of the peak.

It is interesting to note that Eq. (5), derived as the basis for this invention, suggests another means by which the solvent conditions characterizing conditions for which $A_2$ vanishes may be found experimentally. When $A_2=0$, we see that $Mm=I$. Thus $$MK^* \sum_j c_j = \sum_i R_i(0°). \quad (6)$$

In order to find this solvent condition, also known as the theta point, we would measure the two sums for each different solvent and continue to modify the solvent composition until the relation of Eq. (6) is satisfied. It should be obvious, therefore, that there are many additional experimental techniques that are but variations of the methods disclosed herein and that these will be obvious to those trained in the art of light scattering for the characterization of macromolecules.

Accordingly, I claim:

1. A method to determine the $2^{nd}$ virial coefficient of a protein monomer comprising the steps of A) preparing a sample of said protein in a suitable buffering solvent means;
    B) selecting a column set means compatible with said solvent and said protein sample,
    C) connecting said column set sequentially to a multiangle light scattering detector means and a concentration detector means;
    D) providing solvent means reservoir,
    E) providing pumping means by which said solvent means may be made to flow sequentially through said column set, said multiangle light scattering detection means, and said concentration detection means;
    F) injecting an aliquot of said sample onto said column set;
    G) collecting and storing said multiangle light scattering and concentration data in computer means at preselected volumetric incremental intervals, $\Delta v$, throughout said aliquot's elution from said column means and as it passes through said multiangle light scattering and concentration detector means;
    H) forming the sum, by said computer means, $$m = \sum_i c_i$$

from said collected concentration data values, $c_i$, over the entire concentration peak of said protein monomer;

I) forming the sum, by said computer means, $$D = \sum_i c_i^2$$

from said collected concentration data values, $c_i$, over the entire concentration peak of said protein monomer;

J) extrapolating, by said computer means, at each said volumetric incremental interval $\Delta v_j$, said collected multiangle light scattering data to 0° scattering angle to obtain the extrapolated excess Rayleigh ratios $R_j(0°)$;

K) forming the sum, by said computer means, $$I = \sum_j R_j(0°)/K^*$$

from said extrapolated excess Rayleigh ratios $R_j(0°)$ over the entire light scattering peak, where the constant $K^*=4\pi^2(dn/dc)^2 n_0^2/(N_a \lambda_0^4)$, $N_a$ is Avogadro's number, $(dn/dc)$ is the refractive index increment, $n_0$ is the solvent refractive index, and $\lambda_0$ is the wavelength of the incident light in vacuum;

L) calculating, by said computer means, the $2^{nd}$ virial coefficient $$A_2 = \frac{Mm - I}{2M^2 D}$$

where $M$ is the molar mass of said protein monomer.

2. The method of claim 1 where said multiangle light scattering detector means is replaced by a single angle light scattering detector means at angle $\theta$ and said extrapolated excess Rayleigh ratios $R_j(0°)$ are replaced by excess Rayleigh ratios $R_j(\theta)$.

3. The method of claim 2 where said single angle light scattering detector means is at angle $\theta=90°$.

4. The method of claim 1 where said concentration detector means is a differential refractive index, DRI, detector.

5. The method of claim 1 where said concentration detector means is an ultra violet, UV, absorption detector.

6. The method of claim 1 where said concentration detector means is an evaporative light scattering detector.

7. A method to determine the $2^{nd}$ virial coefficient of a monodisperse sample comprising the steps of A) preparing a sample of said monodisperse sample in a suitable solvent means;
    B) selecting a column set means compatible with said solvent and said monodisperse sample;
    C) connecting said column set sequentially to a multiangle light scattering detector means and a concentration detector means;
    D) providing solvent means reservoir;
    E) providing pumping means by which said solvent means may be made to flow sequentially through said column set, said multiangle light scattering detection means, and said concentration detection means;
    F) injecting an aliquot of said sample onto said column set;
    G) collecting and storing said multiangle light scattering and concentration data in computer means at preselected volumetric incremental intervals, $\Delta v$, throughout said aliquot's elution from said column means and as it passes through said multiangle light scattering and concentration detector means;
    H) forming the sum, by said computer means, $$m = \sum_i c_i$$

from said collected concentration data values, $c_i$, over the entire concentration peak of said monodisperse sample;

I) forming the sum, by said computer means, $$D = \sum_i c_i^2$$

said collected concentration data values, $c_i$, over the entire concentration peak of said monodisperse sample, J) extrapolating, by said computer means, at each said volumetric incremental interval $\Delta v_i$, said collected multiangle light scattering data to 0° scattering angle to obtain the extrapolated excess Rayleigh ratios $R_i(0°)$;

K) forming the sum, by said computer means, $$I = \sum_j R_j(0°)/K^*$$

from said extrapolated excess Rayleigh ratios $R_j(0°)$ over the entire light scattering peak, where the constant $K^*4\pi^2(dn/dc)^2 n_0^2/(N_a \lambda_0^4)$, $N_a$ is Avogadro's number, (dn/dc) is the refractive index increment, $n_0$ is the solvent refractive index, and $\lambda_0$ is the wavelength of the incident light in vacuum;

L) calculating, by said computer means, the $2^{nd}$ virial coefficient $$A_2 = \frac{Mm - I}{2M^2 D}$$

where M is the molar mass of said monodisperse sample.

8. The method of claim 7 where said multiangle light scattering detector means is replaced by a single angle light scattering detector means at angle θ and said extrapolated excess Rayleigh ratios $R_j(0°)$ are replaced by excess Rayleigh ratios $R_j(\theta)$.

9. The method of claim 8 where said single angle light scattering detector means is at angle θ=90°.

10. The method of claim 7 where said concentration detector means is a differential refractive index, DRI, detector.

11. The method of claim 7 where said concentration detector means is an ultra violet, UV, absorption detector.

12. The method of claim 7 where said concentration detector means is an evaporative light scattering detector.

13. A method for determining solvent conditions by which the $2^{nd}$ virial coefficient, $A_2$, of a monodisperse sample system is equal to zero comprising the steps of A) preparing a sample of said monodisperse sample in an initial solvent means;

B) selecting a column set means compatible with said solvent and said monodisperse sample;

C) connecting said column set sequentially to a multiangle light scattering detector means and a concentration detector means;

D) providing solvent means reservoir;

E) providing pumping means by which said solvent means may be made to flow sequentially through said column set, said multiangle light scattering detection means, and said concentration detection means;

F) injecting an aliquot of said sample onto said column set;

G) collecting and storing said multiangle light scattering and concentration data in computer means at preselected volumetric incremental intervals, $\Delta v$, throughout said aliquot's elution from said column means and as it passes through said multiangle light scattering and concentration detector means;

H) forming the sum, by said computer means, $$m = \sum_i c_i$$

from said collected concentration data values, $c_i$, over the entire concentration peak of said monodisperse sample;

I) forming the sum, by said computer means, $$D = \sum_i c_i^2$$

from said collected concentration data values, $c_i$, over the entire concentration peak of said monodisperse sample;

J) extrapolating, by said computer means, at each said volumetric incremental interval $\Delta v_i$, said collected multiangle light scattering data to 0° scattering angle to obtain the extrapolated excess Rayleigh ratios $R_i(0°)$;

K) forming the sum, by said computer means, $$I = \sum_j R_j(0°)/K^*$$

from said extrapolated excess Rayleigh ratios $R_j(0°)$ over the entire light scattering peak, where the constant $K^*=4\pi^2(dn/dc)^2 n_0^2/(N_a \lambda_0^4)$, $N_a$ is Avogadro's number, (dn/dc) is the refractive index increment, $n_0$ is the solvent refractive index, and $\lambda_0$ is the wavelength of the incident light in vacuum;

L) calculating, by said computer means, the difference between Mm and I where M is the molar mass of said monodisperse sample;

M) changing the solvent composition and repeating steps A) through L) until such changing composition results in zero difference between said terms Mm and I, said zero difference confirming thereby that said last changed solvent composition corresponds to solvent conditions for which $A_2$ equals zero.

14. The method of claim 13 where said multiangle light scattering detector means is replaced by a single angle light scattering detector means at angle θ and said extrapolated excess Rayleigh ratios $R_j(0°)$ are replaced by excess Rayleigh ratios $R_j(\theta)$.

15. The method of claim 14 where said single angle light scattering detector means is at angle θ=90°.

16. The method of claim 13 where said concentration detector means is a differential refractive index, DRI, detector.

17. The method of claim 13 where said concentration detector means is an ultra violet, UV, absorption detector.

18. The method of claim 13 where said concentration detector means is an evaporative light scattering detector.

19. A method for measuring the $2^{nd}$ virial coefficient of a polydisperse sample comprising the steps of A) preparing a sample of said polydisperse sample in a suitable solvent means;

B) selecting a dilution device whereby a polydisperse sample injected therein is diluted without separation;

C) connecting said dilution device sequentially to a multiangle light scattering detector means and a concentration detector means;

D) providing solvent means reservoir;

E) providing pumping means by which said solvent means may be made to flow sequentially through said column set, said multiangle light scattering detection means, and said concentration detection means;

F) injecting an aliquot of said polydisperse sample into said dilution device means;

G) collecting and storing said multiangle light scattering and concentration data in computer means at preselected volumetric incremental intervals, $\Delta v$, throughout said aliquot' elution from said dilution device means and as it passes through said multiangle light scattering and concentration detector means;

H) forming the sum, by said computer means, $$m = \sum_i c_i$$

from said collected concentration data values, $c_i$, over the entire concentration peak of said polydisperse sample;

I) forming the sum, by said computer means, $$D = \sum_i c_i^2$$

from said collected concentration data values, $c_i$, over the entire concentration peak of said polydisperse sample;

J) extrapolating, by said computer means, at each said volumetric incremental interval $\Delta v_i$, said collected multiangle light scattering data to 0° scattering angle to obtain the extrapolated excess Rayleigh ratios $R_i(0°)$;

K) forming the sum, by said computer means, $$I = \sum_j R_j(0°)/K^*$$

from said extrapolated excess Rayleigh ratios $R_j(0°)$ over the entire light scattering peak, where the constant $K^* = 4\pi^2 (dn/dc)^2 n_0^2/(N_a \lambda_0^4)$, $N_a$ is Avogadro's number, $(dn/dc)$ is the refractive index increment, $n_0$ is the solvent refractive index, and $\lambda_0$ is the wavelength of the incident light in vacuum;

L) calculating, by said computer means, the $2^{nd}$ virial coefficient $$A_2 = \frac{Mm - I}{2M^2 D}$$

where M is the weight average molar mass of said polydisperse sample.

20. The method of claim 19 where said multiangle light scattering detector means is replaced by a single angle light scattering detector means at angle $\theta$ and said extrapolated excess Rayleigh ratios $R_j(0°)$ are replaced by excess Rayleigh ratios $R_j(\theta)$.

21. The method of claim 20 where said single angle light scattering detector means is at angle $\theta = 90°$.

22. The method of claim 19 where said concentration detector means is a differential refractive index, DRI, detector.

23. The method of claim 19 where said concentration detector means is an ultraviolet, UV, absorption detector.

24. The method of claim 19 where said concentration detector means is an evaporative light scattering detector.

* * * * *